United States Patent [19]
Frick et al.

[11] Patent Number: 4,824,242
[45] Date of Patent: Apr. 25, 1989

[54] NON-INVASIVE OXIMETER AND METHOD

[75] Inventors: Gene Frick, Anaheim; Rex McCarthy, Whittier, both of Calif.

[73] Assignee: Sensormedics Corporation, Anaheim, Calif.

[21] Appl. No.: 912,993

[22] Filed: Sep. 26, 1986

[51] Int. Cl.$^4$ .................. G01N 33/49; G01N 21/35
[52] U.S. Cl. ................. 356/41; 364/413.09; 128/633; 128/637; 128/666
[58] Field of Search .......... 356/41; 364/416; 128/633, 637, 666

[56] References Cited

U.S. PATENT DOCUMENTS

| | | | |
|---|---|---|---|
| 2,706,927 | 4/1955 | Wood | 128/633 |
| 3,522,139 | 8/1970 | Coor et al. | 356/97 |
| 3,638,640 | 2/1972 | Shaw | 128/2 R |
| 3,647,299 | 3/1972 | Lavelle | 356/41 |
| 3,799,672 | 3/1974 | Vurek | 356/41 |
| 3,998,550 | 12/1976 | Konishi et al. | 356/39 |
| 4,063,551 | 12/1977 | Sweeny | 128/2.05 P |
| 4,086,915 | 5/1978 | Kofsky et al. | 128/22 |
| 4,167,331 | 9/1979 | Nielson | 356/39 |
| 4,266,554 | 5/1981 | Hamaguri | 128/633 |
| 4,402,290 | 10/1983 | Wilber | 128/633 |
| 4,523,279 | 6/1985 | Sperinde et al. | 364/416 |

FOREIGN PATENT DOCUMENTS

0102816 3/1984 European Pat. Off.
128387 10/1975 Japan .

OTHER PUBLICATIONS

Tait et al., "A Theoretical Analysis of Some Errors in Oximetry" IEEE Transactions on Bio-Medical Engineering, vol. BME-13, No. 4, Oct., 1966.
Wood and Garci, "Photoelectric Determination of Arterial Oxygen Saturation in Man" J. Lab. Clin. Med. 34, pp. 387-401 (1949).
Grover, "Improved Extracorporeal Reflectance Oximeter" Conference Proceedings of the 26th Annual Conference on Engineering in Medicine and Biology, Sep. 30-Oct. 4, 1973, p. 275.
Kramer et al., "Influence of Oxygen Saturation, Erythrocyte Concentration and Optical Depth Upon the Red and Near-Infrared Light Transmittance of Whole Blood" American Journal of Physiology, 165:229-246 (1951).
Schibili et al., "An Electronic Circuit for Red/Infrared Oximeters" IEEE Transactions on Bio-Medical Engineering, vol. BME-25, No. 1, Jan., 1978.

Primary Examiner—Craig E. Church
Assistant Examiner—Jack I. Berman
Attorney, Agent, or Firm—Lyon & Lyon

[57] ABSTRACT

The present invention relates to an oximeter for monitoring oxygen saturation of arterial blood. Light of two wavelengths is transmitted through a specimen. Detectors measure the attenuation of light through the specimen to produce two modulating data streams. The data streams are thereafter processed, evaluated, and compared to determine oxygen saturation. A novel method to process, evaluate and compare the two data streams is disclosed.

5 Claims, 5 Drawing Sheets

OXIMETER HARDWARE BLOCK DIAGRAM

OXIMETER HARDWARE BLOCK DIAGRAM

NON-INVASIVE OXIMETER AND METHOD

BACKGROUND OF THE INVENTION

The present invention relates to a device for measuring the oxygen saturation of arterial blood. More particularly, the present invention relates to an improved non-invasive oximeter and method for mathematically processing the oxygen saturation calculation independent of pulse determination.

Oximetry is the determination of the oxygenation level of the blood. One constituent of human blood is hemoglobin. Hemoglobin which is contained in red blood cells, picks up oxygen from the lungs and carries the oxygen to the body cells. Blood traveling from the lungs to the body cells with oxygen is called arterial blood. Blood traveling to the lungs from the body cells with diminished oxygen is called venous blood. Oximeters function by measuring the oxygen saturation, the amount of oxygenated hemoglobin as a percentage of total hemoglobin, in arterial blood.

The blood oxygen saturation of a patient is one indication of a patient's pulmonary health. In the operating room, blood oxygen saturation is an indication of whether an anesthetized patient is receiving sufficient oxygen. A low oxygen saturation measurement is a warning of dangerous oxygen deprivation, or hypoxemia, a potential cause of injury or death.

Prior to the development of non-invasive oximeters, the oxygen saturation of blood was determined "in vitro", commonly in a container called a cuvette Measurements are first made of the light transmitted through a cuvette filled with a saline solution. This provides a "bloodless" reference measurement for use in the oxygen saturation calculation The cuvette is then filled with blood and a second set of measurements of transmitted light intensity is taken, to provide "blood-filled" measurements at two wavelengths The foregoing measurements of light intensity are converted to absorption values and are then used with standard equations to solve for blood oxygen saturation Once non-invasive oximeters were developed, the necessity of taking blood from the patient was avoided Non-invasive oximeters are now well known and are used widely to measure oxygen saturation Oximeters function by passing light of various colors or wavelengths through a sample. On the human body, typical measuring points are the tip of a finger or an ear lobe. The sample absorbs the transmitted light to varying degrees relative to the particular constituents through which the light passes A photosensitive device, such as a photo multiplier tube or photodiode, is used to detect the transmitted light Alternatively, the photosensitive device can be designed to detect the light reflected from the sample. Either system provides a measure of the light the sample absorbs, i.e., the light the sample does not transmit or reflect Using measurements of the transmitted light intensity, the absorption of light by the sample can be calculated. Calculations can then be made of the percentage of the particular constituent of interest in the sample.

In general, methods for measuring oxygen saturation utilize the relative difference between the light absorption (or attenuation) coefficient of oxygenated hemoglobin and that of reduced hemoglobin. The light absorption coefficient for oxygenated hemoglobin and reduced hemoglobin is dependent on the wavelength of the light traveling through them. Both oxygenated hemoglobin and reduced hemoglobin transmit light having a wavelength in the infrared region to approximately the same degree However, in the visible region, the light absorption coefficient for oxygenated hemoglobin is quite different from the light absorption coefficient of reduced hemoglobin. The two colors typically chosen to shine through the blood sample are red light and infrared light. In oximeters, light intensity is measured at various physiological states The beating of the heart provides the various states. As the heart beats, arterial blood is forced in the arteries and capillaries to produce a blood filled state. The blood then drains leaving a reference which consists of tissue, bone and some amount of venous blood. The collected transmitted light is subjected to photoelectric conversion and then mathematical conversion to eventually calculate the degree of oxygen saturation in the blood.

SUMMARY OF THE INVENTION

The present invention provides an oximeter for non-invasively measuring oxygen saturation of the arterial blood having a light source of at least two wavelengths and a detector or detectors for measuring light intensity after contact with living tissue to produce measurement of at least two light outputs. Circuit means are provided for processing the light output signals and a microprocessor for mathematical evaluation of the signals The processing includes signal separation, noise reduction and amplification. The processed signals are then used to determine a mathematical value, based on the variable strength component of the signal and the steady strength component of the signal for each light output, from which oxygen saturation can be accurately estimated A novel method for determining the variable strength component and the steady strength component of a signal is disclosed.

The recognizable advantage of the disclosed oximeter and method for calculating oxygen saturation is that finding a pulse is unnecessary. In other words, if for any reason pulse detection does not work or is not reliable; a value can still be computed for oxygen saturation. In addition, this method for calculating saturation uses more of the information available in the signal and is less sensitive to noise than is two point calculation o the variable strength signal

BRIEF DESCRIPTION OF THE DRAWINGS

FIG. 5b is the filtered data stream of FIG. 5a.

DETAILED DESCRIPTION OF THE PREFERRED EMBODIMENT

Figure 1:
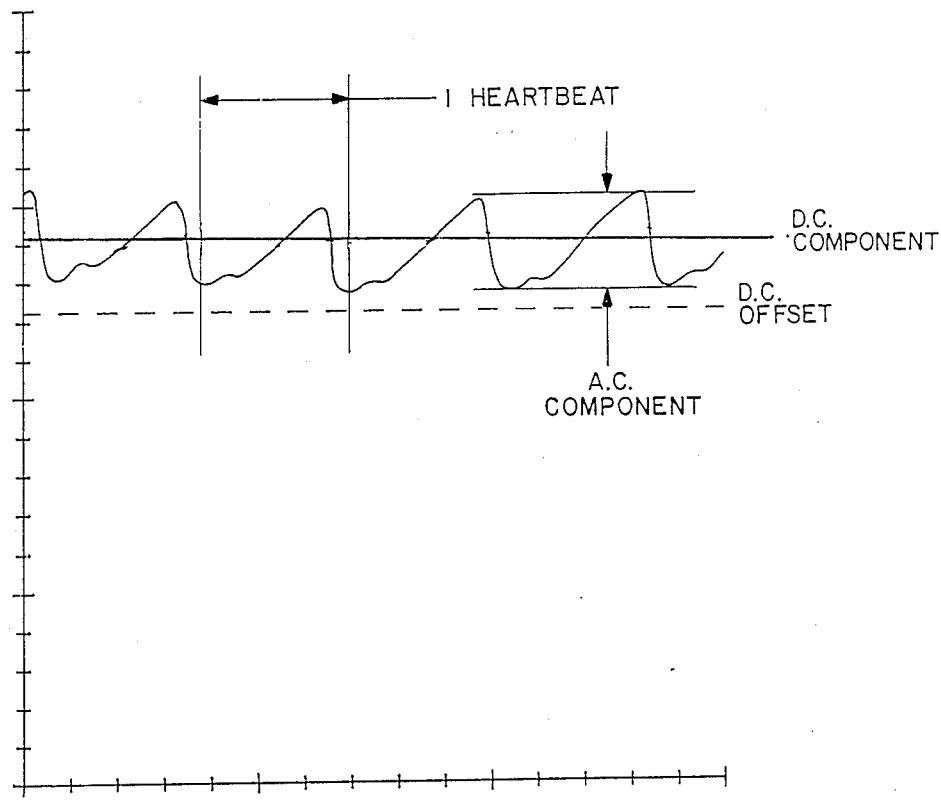
FIG. 1 is a data stream showing the A.C. component, the D.C. component, and the D.C offset.

The invention can be best understood by first examining typical analog signals or values of the data points in the data streams following the analog to digital conversion, outputting from the photo detectors or photodiodes. In each instance, FIGS. 1–5b, the y-axis represents the electrical signal, e.g., voltage, and the x-axis represents time. FIG. 1 depicts a relatively noise free data stream without a baseline drift. The data stream comprises a DC component and an AC component. The DC component further comprises a DC offset and DC remainder. The AC component relative to the DC component, is small. To simplify the evaluation of the AC signal, necessary for the determination of oxygen saturation, the DC offset is removed. The remaining signal is thereafter amplified. The data stream of FIG. 1 after removal of the D.C. offset and amplification is shown in FIG. 2.

Figure 2:
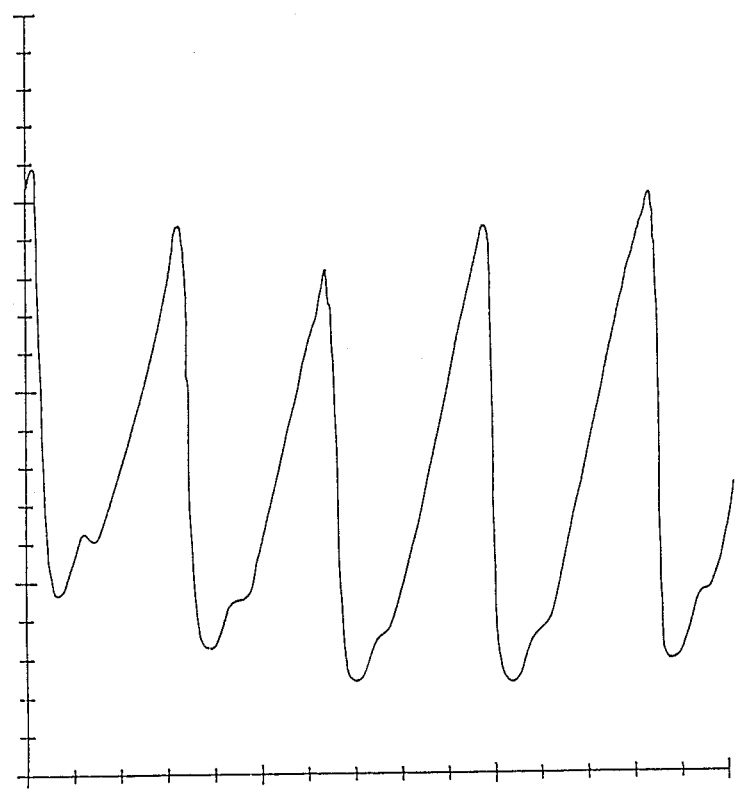
FIG. 2 is the data stream of FIG. 1 following removal of the D C. offset and following amplification.
Figure 3:
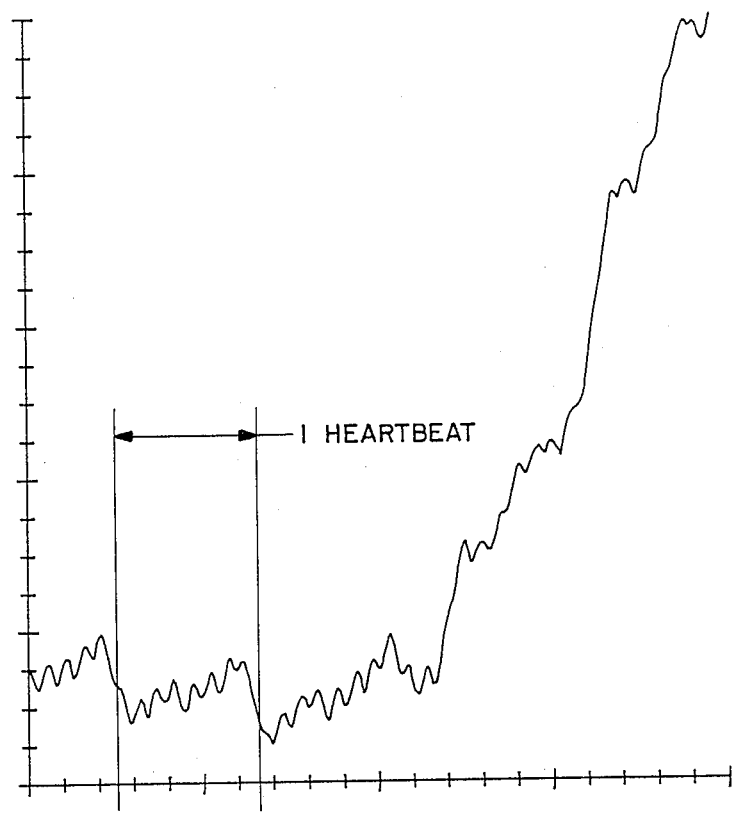
FIG. 3 is a noisy data stream with a complicating feature known as baseline drift.
Figure 4:
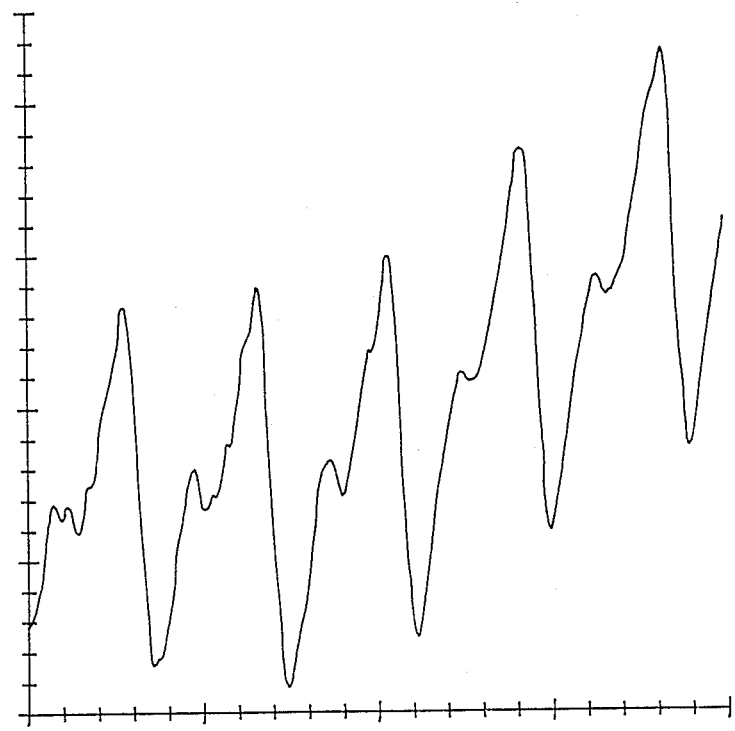
FIG. 4 is a data stream following removal of the D.C. offset and following amplification with a complicating feature known as a dicrotic notch.
Figure 5A:
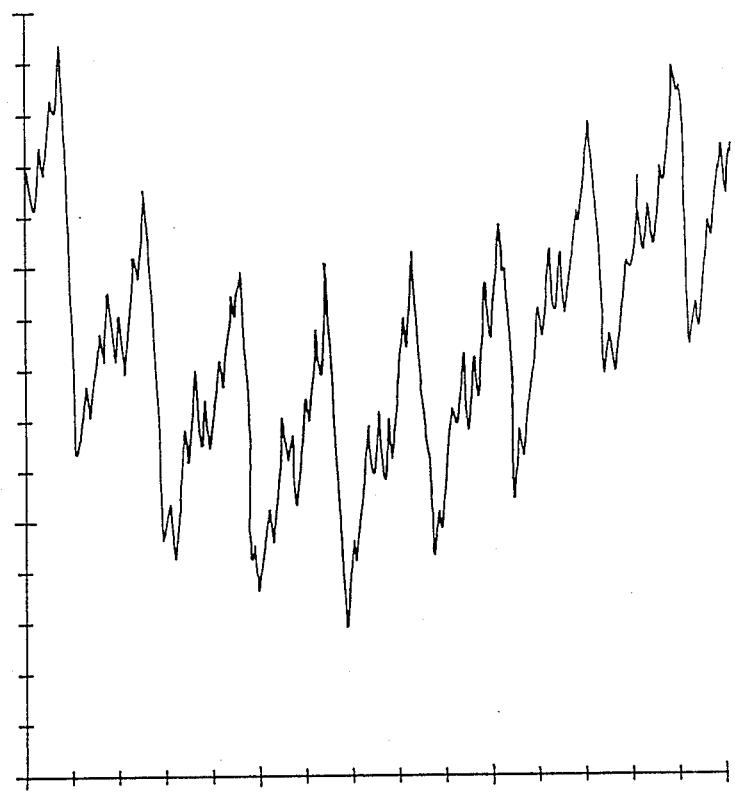
FIG. 5a is a data stream similar to FIG. 4, but with substantial noise.

The signal of FIGS. 1 and 2 is a relatively clean data stream. However, many data streams outputting from the photo detectors are substantially more complicated. FIG. 3 depicts a complex data stream, that is both noisy and has a substantial baseline drift. Another data stream, shown in FIG. 4, following removal of the DC offset and following amplification has a complicating feature known as a dicrotic notch. The data stream of FIG. 5a is similar to that shown in FIG. 4. However, the FIG. 5a data stream has the additional complicating factor of a high noise level.

The operating principles of the oximeter are described first. One theory of pulse oximetry holds that blood oxygen saturation can be calculated from the ratio of two measurements of light attenuation made at each of two wavelengths. The two measurements form a fraction, based on Lambert-Beer's law, with the variable strength component of the data stream signal being the numerator and the steady strength component of the data stream signal being the denominator, for each of the two wavelengths.

It has been learned that the variable strength component of the signal can be approximated by the sum of the deviation of the data stream from the mean of the data stream over a period of time. This is very similar to the determination of root mean squared measurements of the AC component of the data stream. One definition for root mean squared is the average of the absolute deviation from the mean. However, division to find the average of a ratio, as required by the oxygen saturation calculation, is not necessary. If $2N+1$ represents the number of discrete data points over the period of time of interest, the mean at a given time $t_i$ is calculated using the relationship:

$$\overline{P_i} = \frac{\sum_{j=1}^{N}(P_{i+j} + P_{i-j})}{2N}$$

Where $P_{i+j}$ is the data stream value at time $t_i+t_j$ and $P_{i-j}$ is the data stream value at time $t_i-t_j$.

Once the first mean value is determined, successive means are determined by the following formula:

$$\overline{P_{i+1}} = \overline{P_i} + \frac{P_{i+1+N}}{2N} - \frac{P_{i-N}}{2N}$$

Which is to say that after the first mean is calculated succeeding means are found by taking the value of the preceding mean and adding the leading data point in the data stream divided by 2N and then subtracting the trailing data point for the preceding mean calculation divided by 2N where the new and old points are separated by 2N points.

For the oxygen saturation calculation, the approximated steady strength component of the signal, DCI, is the sum of the mean and the DC offset. The approximated variable strength component of signal, or TIRMS, is:

$$TIRMS = \sum_i ABSV(P_i - \overline{P_i})$$

ABSV represents the determination of the absolute value of the difference between $P_i$ and $\overline{P_i}$. The TIRMS value is thus a running sum for a series of absolute values. Each absolute value in the series is the difference between the mean value and the data point value at a discrete moment in time. When an oxygen saturation calculation is required, the TIRMS value can be, but need not be, reset to zero.

Once TIRMS-A and DCI-A, representing the A channel, and TIRMS-B and DCI-B, representing the B channel, are determined a RATIO is calculated:

$$RATIO = \frac{\frac{TIRMS\text{-}A}{DCI\text{-}A}}{\frac{TIRMS\text{-}B}{DCI\text{-}B}}$$

In general, it is conceded that Lambert-Beer's law type absorption and light scattering by red cells determines the nature of the signals received by the detector in a typical pulse oximeter transducer. This being the case, it seems reasonable to use quantities suggested by Lambert-Beer's law as the basis for the oxygen saturation calculation. However, it has been learned that whole blood does not obey Lambert-Beer's law. Therefore, the value of RATIO is not used directly to calculate oxygen saturation. Rather, both the RATIO and empirically determined data are used as the basis for making the oxygen saturation calculation. A more accurate relationship between RATIO and the actual oxygen saturation has been determined by taking actual measurements of oxygen saturation of blood and comparing these measurements with the value of RATIO taken simultaneously. A second order polynomial fit of the data is made. The polynomial coefficients are dependent on the wavelength of the transmitted light and several sets of coefficients can be determined as required.

The value of oxygen saturation is thus:

$$\% SaO_2 = a + (b \times RATIO) + (c \times (RATIO)^2)$$

where a, b and c are numbers fixed for various wavelengths.

A novel wave form filter based on the following principles can be incorporated as part of the oximeter Associated with every given data point in the data stream and equidistant from that data point are multiple pairs of data points. That is, each data point has multiple pairs of associated data points. For each pair, the first associated data point occurs some time prior to the given data point and the second associated data point occurs an equal amount of time after the given data point. A difference is found by subtracting the detected values for the associated data points one from another. The difference for each pair of associated data points is then summed to form the output of a wave form filter for the given point. The total time spanned by these associated points is called the wave form filter length. This can be expressed in the following fashion:

$$F_i = \sum_{j=1}^{L} (P_{i+j} - P_{i-j})$$

Where $F_i$ is the wave form filter output for a given time $t_i$ having a data stream value $P_i$, $P_{i-j}$ is the data stream value at time $t_i-t_j$; $P_{i+j}$ is the data stream value at time $t_i+t_j$; and the wave form filter length is $2*L+1$. Using this approach to finding $F_i$ requires L subtractions and $L-1$ additions.

A simpler calculation of $F_{i+1}$ is possible if $F_i$ has already been computed. That is:

$$F_{i+1} = F_i + P_{i+L+1} + P_{i-L} - P_i - P_{i+1}$$

This calculation requires only two additions and two subtractions regardless of the length of the wave form filter. Present microprocessors are able to make this calculation in real time if the discrete points in the data stream occur at, for example, 15 millisecond intervals. For this calculation, memory of $2L+1$ values is required.

The accuracy of the output of the wave form filter for pulse detection is best when the wave form filter length and the pulse length of the signal are the same. When there is a large mismatch in these two quantities, the accuracy of the filter is diminished. Two methods have been found to overcome this problem. The first is to use two or more filters and examine each of them separately to determine which most closely matches the pulse length. The other is to combine two filters such that their combined output will work on any signal of interest. The second method requires four additions and four subtractions for each point.

Figure 5B:
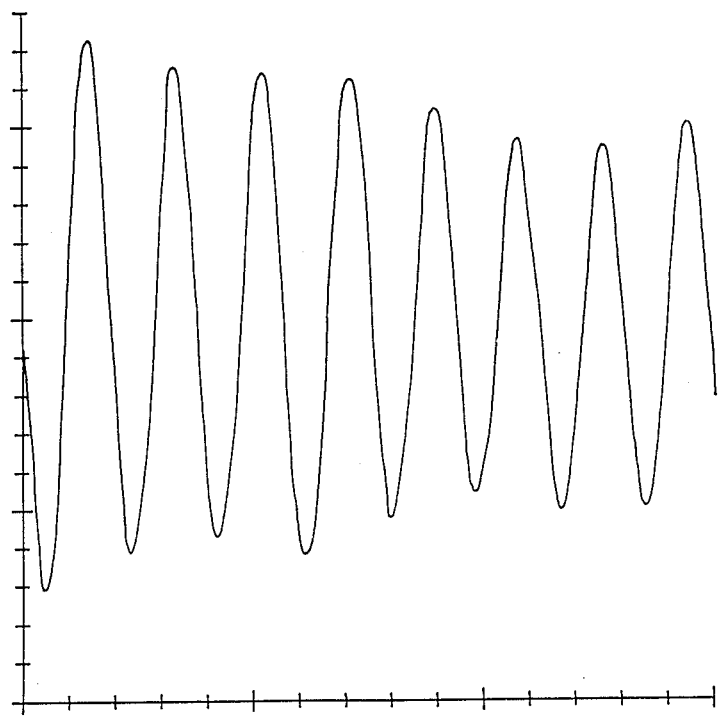

FIG. 5b depicts the data stream of FIG. 5a after filtering. Clearly, the filtering of the data stream eases the pulse determination.

The amplitude of the output from the wave form filter has been found substantially proportional to the variable signal. The output is therefore useful in the calculation of oxygen saturation if both an A channel and a B channel are filtered.

Figure 6:
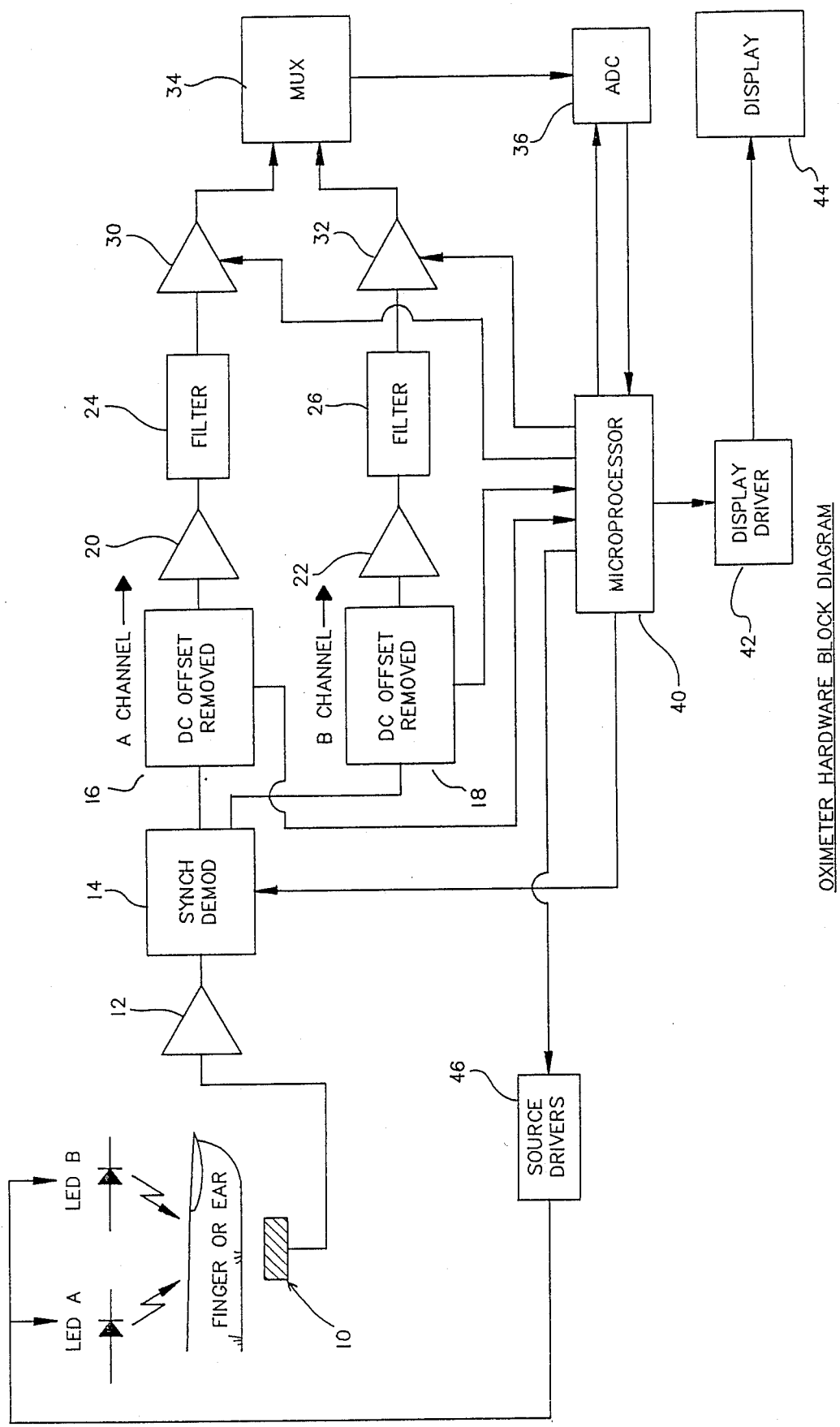
FIG. 6 is a block diagram of the oximeter and wave form filter.

The functioning of the oximeter and the wave form filter is now described. In FIG. 6, there is depicted a schematic representation of the present invention. A photoelectric transducer or photodiode 10 receives the light transmitted through a measuring point in the human body such as an ear lobe or finger. Two light components are transmitted through the measuring point. Light component A is transmitted from LED A and light component B is transmitted from LED B. Both light component A and light component B are selected for their relative light attenuation in oxygenated hemoglobin and reduced hemoglobin. In reduced hemoglobin, the attenuation coefficients of the two light components are substantially different. Typically red light and infrared light will comprise these light components.

The data streams detected by photodiode 10 are amplified by pre-amplifier 12 and passed through the synchronized demodulator 14 to separate the data streams for each of the two light components. For each of the two data streams, the data stream is further separated (16 and 18) into a DC offset and the DC remainder plus the AC component. The values of the DC offset are sampled and held in the microprocessor 40 for further processing. Alternatively, the DC offset can be preset at a fixed value. Once the DC offset is removed, data streams A and B are passed through operational amplifiers 20 and 22. The signal streams are amplified by fixed gains relative to the signal strengths of channel A and channel B. If the A channel processes the red signal, the fixed gain may be approximately a multiple of 200–250 of the preexisting data stream while, the B channel, if processing an infrared signal, the fixed gain may be approximately a multiple of 40–60 of the preexisting data stream.

The data streams of both channels A and B are passed through filters 24 and 26 to reduce gross extraneous noise. The signal streams are then passed through variable attenuators 30 and 32, the control of which is performed by an evaluation of the signal strength made by the microprocessor 40. The signal streams are then inputted to multiplexor of 34 where they are sampled and held until the analog to digital convertor 36 has converted each incoming analog signal into an outgoing digital signal.

Figure 7:
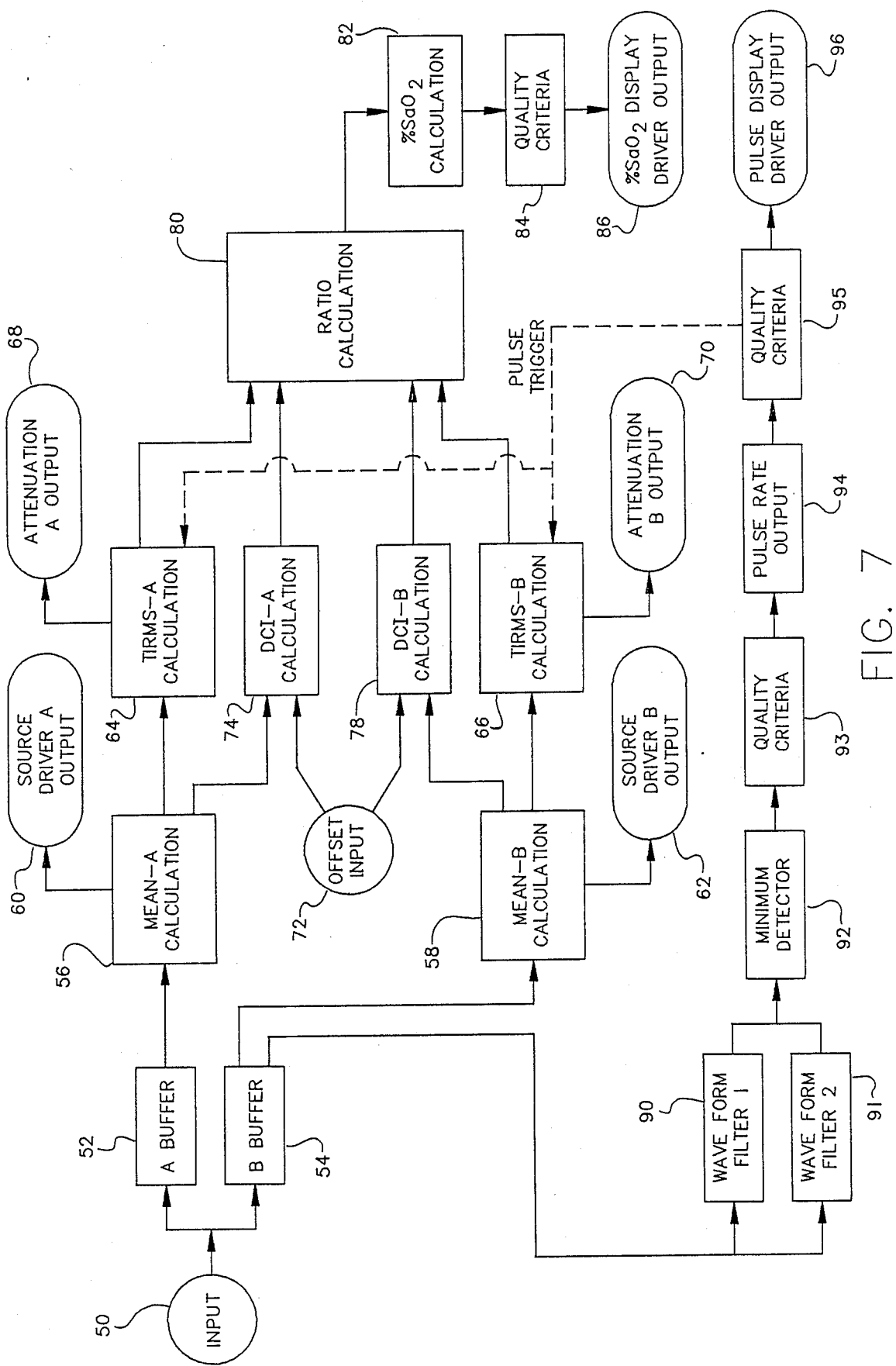
FIG. 7 is a process flow block diagram of the microprocessor unit of the oximeter and wave form filter.

The data streams are thereafter processed as shown in FIG. 7. As each data point in the data stream is inputted into the microprocessor 40, they are stored in buffers 52 and 54. As inputs are received the values are sequentially stored in the buffers replacing previous values which are shifted through and eventually out of the buffers. When the process is first started or after data is lost, the microprocessor 40 holds until the buffer is full before commencing a calculation.

Once the buffers fill, the wave form filter or filter outputs, if more than one wave form filter is used, are calculated (90, 91). The initial wave form filter output is determined by subtracting each successive trailing data point in the data stream from each successive leading data point in the data stream and then summing values. Each successive wave form filter output is determined by summing (i) the most recent wave form filter output, (ii) the trailing data point in the data stream, and (iii) the leading data point in the data stream for the most recent wave form filter output calculation and subtracting the sum of (i) the data point in the data stream halfway through the buffer and (ii) the data point in the data stream one data point beyond the halfway mark in the buffer. The foregoing mathematical calculation is performed for each wave form filter used.

Once the wave form filter outputs are determined, a detector 92 is used to determine an extreme value, such as a maximum or minimum. The rate of the extreme values are compared (93), by using quality criteria, with an expected range of values. If the extreme value is within the range of expected values, the pulse rate is determined (94). The pulse rate is also compared (95), by using quality criteria, with an expected range of pulse rates. If the pulse rate is within the range of expected values, the pulse rate is outputted to the pulse display driver (96).

Simultaneously, the mean values are calculated (56, 58). The initial mean values for both channels A and B are determined by summing the values of the data points in the buffer and dividing by the number of data points in the buffer. After the initial mean values are calculated, additional mean values are determined by adding the most recent mean value to the value of the trailing data point in the data stream, divided by the number of data points in the buffer, and then subtracting the value of the trailing data point for the most recent mean value calculation divided by the number of data points in the buffer. Once MEAN-A and MEAN-B are known, TIRMS-A and TIRMS-B are calculated (64, 66). The mean value is subtracted from the value of the data point halfway through the buffer to obtain a data stream comprising intermediate values. The absolute value of the intermediate values are then summed to obtain TIRMS-A and TIRMS-B.

The TIRMS-A and TIRMS-B values comprise the numerators of the ratios used in the RATIO calculation. The mean value is also used to determine the denominators in the ratio calculation. The denominators, referred to as DCI-A and DCI-B are calculated (74, 78) by summing, separately for each channel, the mean value and the D.C. offset.

The RATIO calculation is thereafter performed (80). By using the RATIO, oxygen saturation can be calculated (82). The oxygen saturation calculation is compared (84), by using quality criteria, with an expected range of values. If the oxygen saturation is within the range of expected values, the oxygen saturation is outputted to the oxygen saturation display driver (86).

A triggering mechanism can be incorporated in the oximeter to initiate each successive oxygen saturation calculation or an antecedent calculation required for each successive oxygen saturation calculation. The triggering mechanism can be a timer or equivalent means. Alternatively, if the wave form filter is incorporated as part of the oximeter, then the detection of a pulse can be used as the triggering mechanism.

The TIRMS and mean values are also useful in control of the instrument. From time to time the microprocessor will adjust the signal strength by increasing or decreasing the light level being emitted by the LEDs. Adjustments in the signal strength are necessary because the analog to digital converter has a limited range, required by the need for precision and sensitivity in the oxygen saturation calculation. The signal strength will be adjusted when mean value exceeds an upper or a lower limit. A signal to the source driver 46 is outputted by the microprocessor 40 by either channel A or B (60, 62).

The size of the AC component of the signal relative to the size of the analog to digital conversion range is used to control the variable attenuators (30, 32). If the AC component of the signal is relatively small, the signal will be sensitive to digitizing noise resulting in a loss of accuracy. If the AC component of the signal is relatively large, baseline drift or other signal variations will cause the signal to move outside of the range of the analog to digital convertor prompting a change in the drive current to the LEDs. Changing the drive current to the LEDs is less desirable than simply attenuating the signal. The attenuators are controlled by the microprocessor 40. This control function uses the TIRMS value to determine when attenuation of the signal is required. If so, a signal is outputted from the microprocessor by either channel A or B (68, 70).

While the above embodiments have been disclosed as the best mode presently contemplated by the inventor, it should be realized that these examples should not be interpreted as limiting, because an artisan skilled in this field, once given the present teachings, can vary from these specific embodiments. Accordingly, the scope of the present invention should be determined solely from the following claims.

We claim:

1. An oximeter for non-invasively measuring oxygen saturation of the arterial blood comprising:
    means for transmitting light of two wavelengths through a specimen,
    means for monitoring the transmitted light to produce at least a first and second data stream comprising a series of values representative of the attenuation of light by the specimen over time,
    means for storing the series of values for each data stream, whereby each of the stored values is a discrete moment in time and the stored values are continually updated over time,
    means for evaluating the stored values separately for each data stream, comprising a means for determining over time a series of quantities, each quantity substantially equivalent to the mean of the stored values at that time, and a means for determining the deviation of the series of quantities from the series of stored values, and
    means for comparing the deviation of the data streams.

2. The oximeter of claim 1 further comprising a wave form filter to determine pulses wherein the occurrence of pulses triggers the operation of the means for evaluating the stored values.

3. The oximeter of claim 1 further comprising a timer whereby the occurrence of time intervals triggers the means for evaluating the series of stored values.

4. The oximeter of claim 1 further comprising a wave form filter for filtering the first and second data streams.

5. A method for non-invasively determining the oxygen saturation of arterial blood, comprising:
    transmitting light of two wavelengths through a specimen,
    monitoring the transmitted light to produce a first and second data stream comprising a series of values representative of the attenuation of light by the specimen over time,
    storing the series of values for each data stream, whereby each of the stored values is a discrete moment in time,
    updating the series of stored values continually over time,
    evaluating the series of stored values separately for each data stream by determining over time a series of quantities, each quantity substantially equivalent to the mean of the series of stored values at that time, and by determining the deviation of the series of quantities from the series of stored values, and
    comparing the deviations of the data streams.

* * * * *